(12) United States Patent
Christ et al.

(10) Patent No.: US 11,466,243 B2
(45) Date of Patent: Oct. 11, 2022

(54) BIOREACTOR CONTROLLER DEVICE AND RELATED METHOD THEREOF

(71) Applicant: University of Virginia Patent Foundation, Charlottesville, VA (US)

(72) Inventors: George Christ, Crozet, VA (US); Joshua David Remer, Charlottesville, VA (US); Gavin T. Garner, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 917 days.

(21) Appl. No.: 16/322,691

(22) PCT Filed: Aug. 3, 2017

(86) PCT No.: PCT/US2017/045299
§ 371 (c)(1),
(2) Date: Feb. 1, 2019

(87) PCT Pub. No.: WO2018/027033
PCT Pub. Date: Feb. 8, 2018

(65) Prior Publication Data
US 2021/0348112 A1    Nov. 11, 2021

Related U.S. Application Data (60) Provisional application No. 62/370,331, filed on Aug. 3, 2016.

(51) Int. Cl.
*C12M 1/36* (2006.01)
*G05B 19/042* (2006.01)
*G05B 23/02* (2006.01)

(52) U.S. Cl.
CPC .......... *C12M 41/48* (2013.01); *G05B 19/042* (2013.01); *G05B 23/0272* (2013.01); *G05B 2219/25257* (2013.01); *G05B 2223/06* (2018.08)

(58) Field of Classification Search
CPC ...... C12M 41/48; G05B 19/42; G05B 19/042; G05B 2219/25257; G05B 2223/06; G06F 9/44
See application file for complete search history.

(56) References Cited

U.S. PATENT DOCUMENTS

| 5,795,710 A | 8/1998 | Park | |
|---|---|---|---|
| 7,989,199 B2 * | 8/2011 | West | C12Q 3/00 239/66 |

(Continued)

FOREIGN PATENT DOCUMENTS

| CN | 100525063 C | 8/2009 | |
|---|---|---|---|
| EP | 2500410 A1 * | 9/2012 | ............ C12M 21/08 |
| WO | 2016/036764 A2 | 3/2016 | |

OTHER PUBLICATIONS

Office Action dated Apr. 7, 2020, issued in counterpart EP Application No. 17837684.4 (1 page).

(Continued)

*Primary Examiner* — Vincent H Tran
(74) *Attorney, Agent, or Firm* — WHDA, LLP (57) ABSTRACT

The present invention provides a bioreactor controller with a simple user interface comprising a microcontroller and a linear motor. The bioreactor controller is microcontroller-based, has a greater temporal accuracy, and inexpensive. The microcontroller of the bioreactor controller selects a protocol mode and a setup mode by the user, runs the protocol mode if the setup mode is not selected by the user, stops running the protocol mode for a predetermined time if the protocol mode is selected by the user until the user is (Continued)

completed with calculations and record-keeping, detects movement error of the bioreactor controller, and informs the error to the user.

18 Claims, 6 Drawing Sheets

(56) References Cited

U.S. PATENT DOCUMENTS

| | | | |
|---|---|---|---|
| 2005/0153436 A1* | 7/2005 | Vilendrer | C12M 35/04 435/289.1 |
| 2007/0188117 A1* | 8/2007 | Shoda | H02P 25/06 318/135 |
| 2009/0265005 A1 | 10/2009 | Yoo et al. | |
| 2012/0086657 A1 | 4/2012 | Stanton, IV et al. | |
| 2018/0228144 A1* | 8/2018 | Bonvillain | A01N 1/0247 |

OTHER PUBLICATIONS

Extended (Supplementary) European Search Report dated Mar. 19, 2020, counterpart to EP Application No. 17837684 4. (6 pages).

International Search Report dated Oct. 20, 2017, issued in counterpart application No. PCT/US2017/045299 (2 pages).

Written Opinion dated Oct. 20, 2017, issued in counterpart application No. PCT/US2017/045299 (4 pages).

* cited by examiner

BIOREACTOR CONTROLLER DEVICE AND RELATED METHOD THEREOF

TECHNICAL FIELD

The present invention provides a controller device (and related method) for precise, accurate, and reliable bioreactor operations at an extremely low cost.

BACKGROUND ART

Biomechanical signals are important for developing muscle cells. Cyclic mechanical stretch alters the phenotypic characteristics of muscle progenitor cells (MPCs), and perhaps more importantly, significantly improves functional muscle regeneration when engineered constructs are implanted in biologically relevant rodent models of volumetric muscle loss (VML) injury. Thus, bioreactor preconditioning is an integral portion of our tissue-engineered muscle implant manufacturing protocol.

Technical Problem

The old system for a bioreactor controller requires one PC for each controller. In addition, its software is unstable, and the cost ($400-$1,000) for the old system is high. Finally, the old system is temporally inaccurate (1 hour/week drift). Therefore, there is a need for a new system that is independent of PC and inexpensive. Also, the software for the new system should be stable.

Solution to Problem

The present invention provides a custom designed device that utilizes linear stepper motor technology to accomplish cyclic stretching for eight scaffolds at a time while being durable enough to endure sterilizations and constant use. The present invention provides a way of digital control for the bioreactor via an in-house designed microcontroller-based system called BrC.

In particular, the present invention provides a controller device that is microcontroller-based and has a greater temporal accuracy (less than 1 second/week). Here, the cost of the controller device is significantly lower than that of the old system, and its software is very stable.

SUMMARY OF INVENTION

The first aspect of the present invention defines a microcontroller-based bioreactor controller with a simple user interface, controlling a linear stepper motor on a bioreactor system. The interface is designed such that customizable protocol parameters can be selected, or if normal operation is desired, default values will be applied without requiring the user to enter a setup mode. Additionally, the bioreactor controller is equipped with a movement-error detection feature capable of informing the user when the motor has not moved according to software commands.

According to the first aspect of the present invention, the movement error detection is performed by a digital differential encoder, and the error signal is processed within the microcontroller.

According to the first aspect of the present invention, the encoder determines whether a shaft of the linear motor of the bioreactor controller moves according to an input command by the user.

According to the first aspect of the present invention, temporal accuracy is less than 1 second per week.

According to the first aspect of the present invention, resolution of the linear motor is less than 5 µm.

The second aspect of the present invention defines a method for a bioreactor controller with a simple user interface, the bioreactor controller comprising a microcontroller and a linear motor, comprising the steps of selecting a protocol mode and a setup mode by the user, running the protocol mode if the setup mode is not selected by the user, stopping running the protocol mode for a predetermined time if the protocol mode is selected by the user until the user is completed with calculations and record-keeping, detecting movement error of the bioreactor controller, and informing the error to the user.

According to the second aspect of the present invention, the detecting movement error is performed by an encoder.

According to the second aspect of the present invention, a digital, optical, or differential encoder is mounted onto a shaft of the linear motor.

According to the second aspect of the present invention, the encoder determines whether a shaft of the linear motor of the bioreactor controller moves according to an input command by the user.

According to the second aspect of the present invention, temporal accuracy is less than 1 second per week.

According to the second aspect of the present invention, resolution of the linear motor is less than 5 µm.

The third aspect of the present invention defines a non-transitory computer readable medium storing a program causing a computer to execute a method for a bioreactor controller with a simple user interface, the bioreactor controller comprising a microcontroller and a linear motor, the method comprising the steps of selecting a protocol mode and a setup mode by the user, running the protocol mode if the setup mode is not selected by the user, stopping running the protocol mode for a predetermined time if the protocol mode is selected by the user until the user is completed with calculations and record-keeping, detecting movement error of the bioreactor controller, and informing the error to the user.

According to the third aspect of the present invention, the detecting movement error is performed by an encoder.

According to the third aspect of the present invention, a digital, optical, or differential encoder is mounted onto a shaft of the linear motor.

According to the third aspect of the present invention, the encoder determines whether a shaft of the linear motor of the bioreactor controller moves according to an input command by the user.

According to the third aspect of the present invention, temporal accuracy is less than 1 second per week.

According to the third aspect of the present invention, resolution of the linear motor is less than 5 µm.

Advantageous Effects of Invention

The present invention provides a controller device that is microcontroller-based, inexpensive. The controller device has a greater temporal accuracy. Its software is very stable, provides a simple user interface, and enables the user to modify the existing program to add functionalities easily.

DESCRIPTION OF EMBODIMENTS

Figure 1:
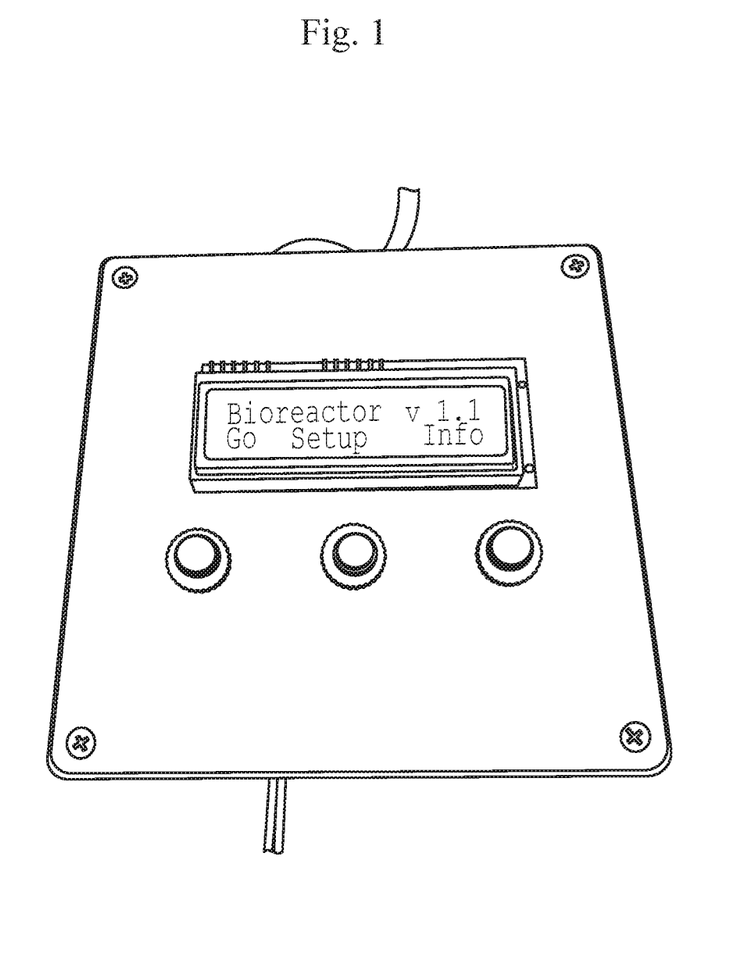
FIG. 1 shows a bioreactor controller in accordance with one embodiment of the present invention.

In the first embodiment, the present invention provides a controller device (FIG. 1) with only three buttons, for example, for controlling all selection parameters. BrC operation is very simple and highly intuitive. Upon powering up the BrC (accomplished simply by plugging in a 12V power source), the user can either immediately begin the protocol or enter setup mode. The BrC (and related method) allows its user to select a stretch distance, protocol duration, and linear motor from its simplified user interface.

In another embodiment, all variables are preset in normal design iteration. Thus, if the user does not enter the setup phase, the BrC will run according to the normal experimental protocol. When the protocol is started, the BrC will wait until the next minute to begin. This simplifies calculations and record-keeping for the researcher. In a default operation, the BrC will move the bioreactor out 3 mm, then in 3 mm over 20 seconds. A total of 15 repetitions of this motion occur over 5 minutes. The BrC then waits 55 minutes and repeats this process for 120 hours. Other durations and intervals may be implemented.

Figure 4:
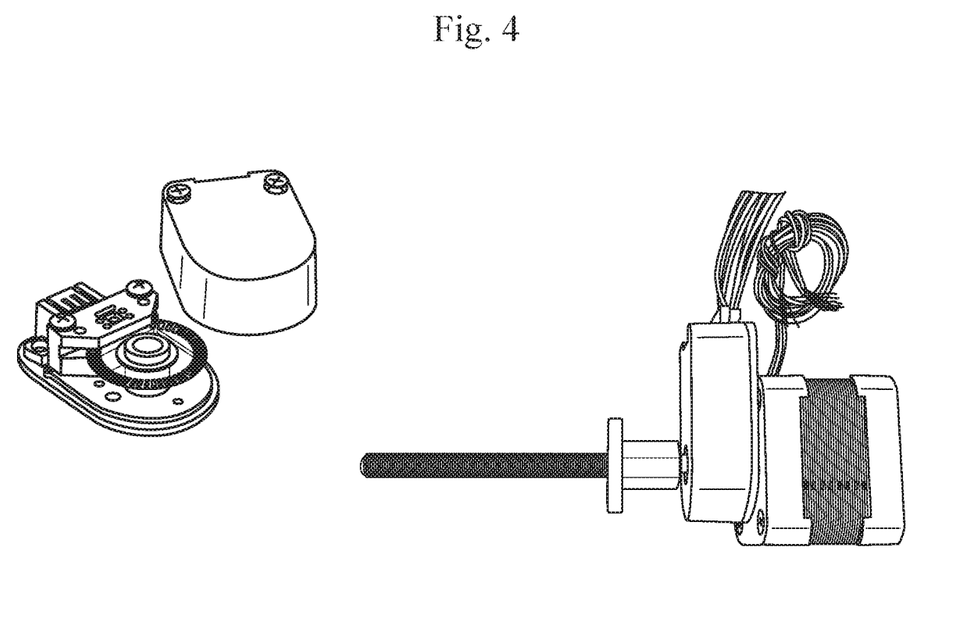
FIG. 4 shows a movement error detection mechanism for the bioreactor controller in accordance with another embodiment of the present invention.

In another embodiment, an additional feature provided to the BrC involves movement error recognition by means of an encoder (FIG. 4). This movement error recognition ensures that the controller device moves according to software commands. The digital, optical, differential encoder is mounted onto the shaft of the linear motor, and counts 400 indications per revolution. If the encoder sends a significantly different number of counts (i.e., currently roughly 1% difference), it means that the motor shaft has not accurately followed the software commands, and that the scaffold was not stretched accordingly. The microcontroller will register this as an error and inform the user as such. Not all BrCs will implement the encoder technology. However, with the newest printed circuit board (PCB) circuit design, the capability exists for it to be mounted post-hoc.

Hardware

Figure 3:
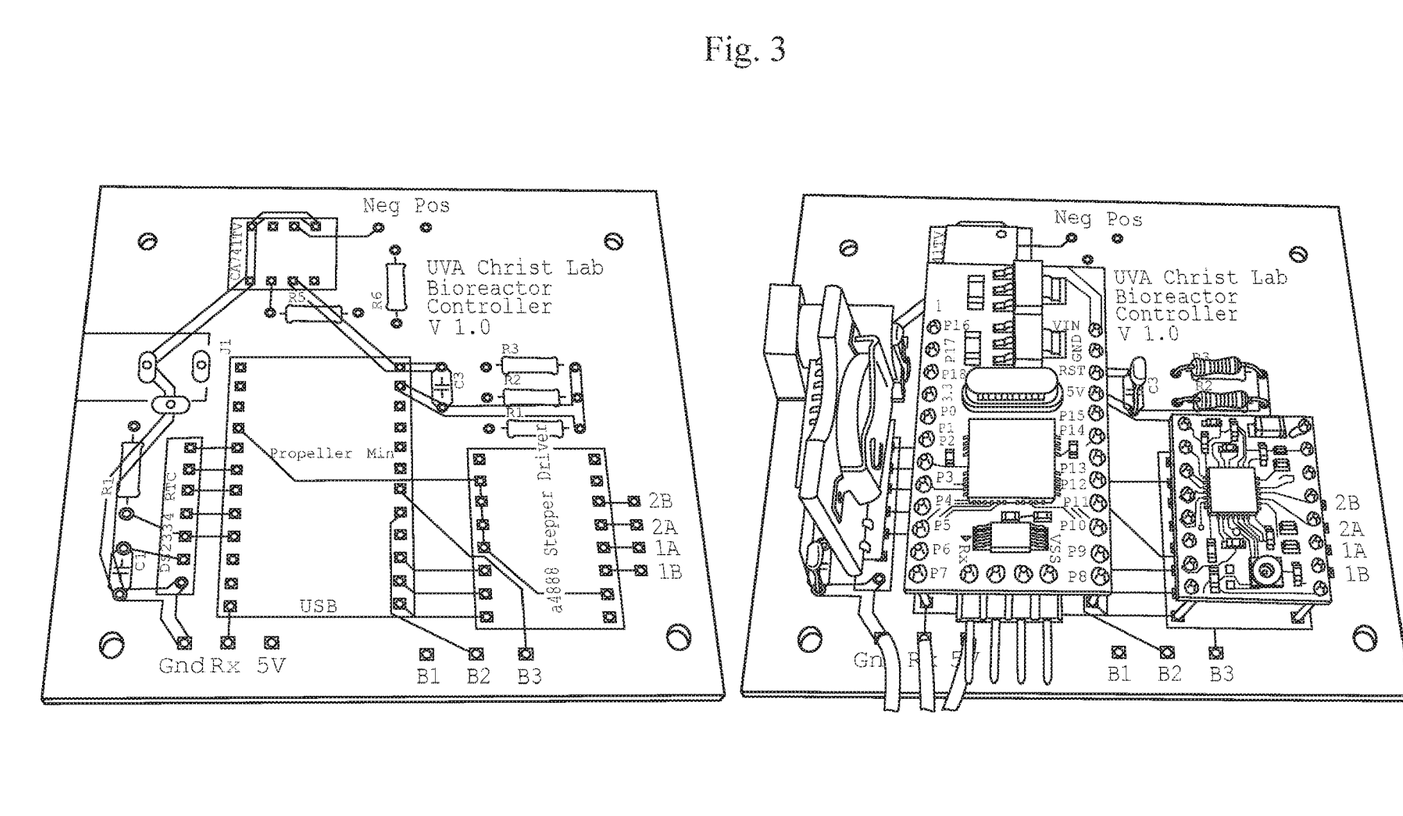
FIG. 3 shows various components mounted onto the PCB for the bioreactor controller in accordance with another embodiment of the present invention.

All components of the BrC are listed in the table below (Table 1). FIG. 3 shows various components mounted onto the PCB. The present invention provides the controller device implemented on the PCB, where durability is significantly increased, and assembly time is reduced. In addition, the cost is significantly lower than that of the old system. For example, the cost for the PCB is about $10, and the cost for the assembled device is about $150. Another strength of the BrC is, but not limited thereto, its excellent resolution across its several systems. For example, the controller device is capable of high precision motion (0.25 μm; preferably 10 μm steps). Also, the controller device has an excellent temporal resolution, for example, less than 1 minute per year. These are shown in the table below (Table 2).

Figure 5:
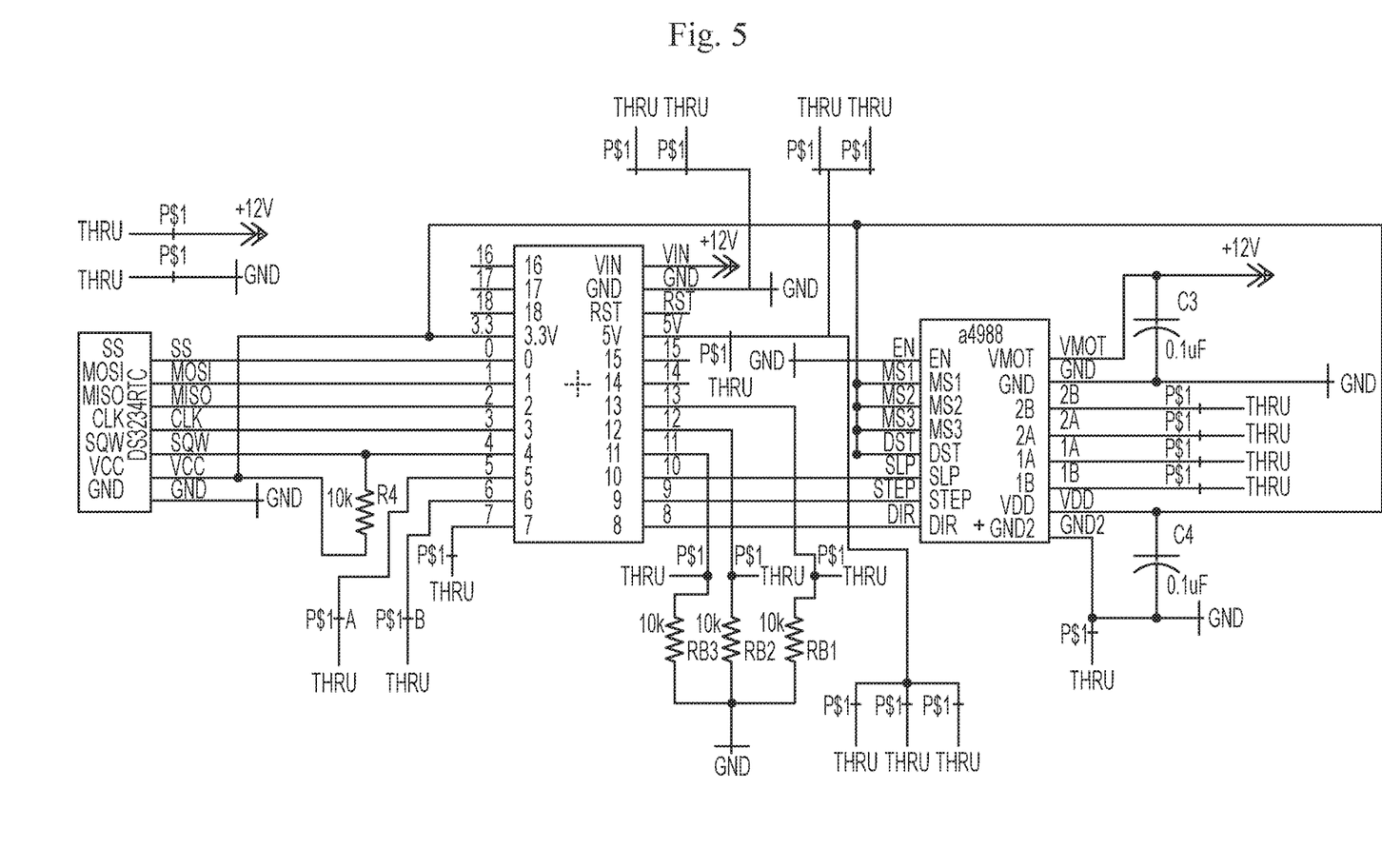
FIG. 5 shows a circuit diagram of the PCB design for the bioreactor controller in accordance with another embodiment of the present invention.
Figure 6:
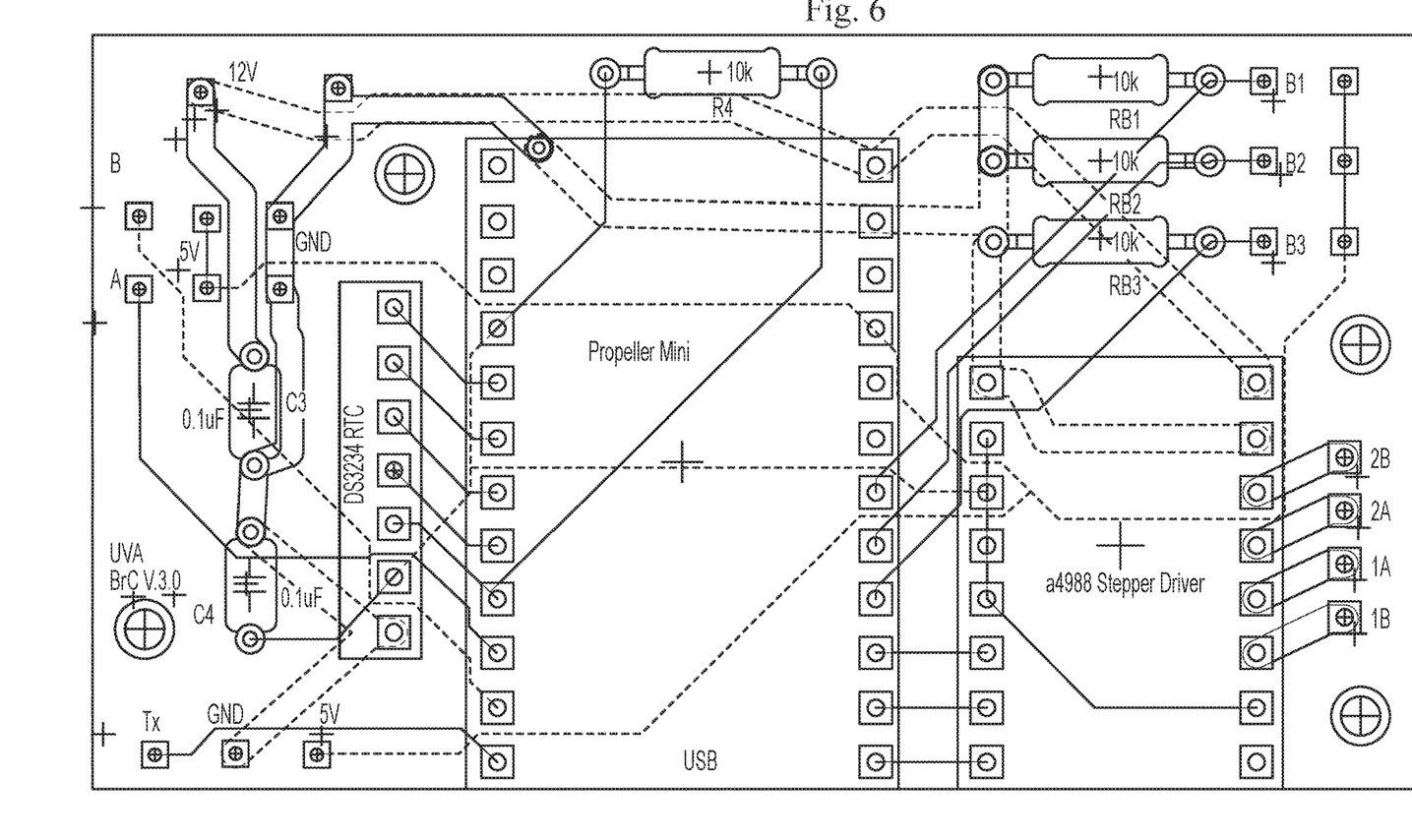
FIG. 6 shows a physical layout of the PCB design for the bioreactor controller in accordance with another embodiment of the present invention.

The PCB physical layout (FIG. 6) is designed with CadSoft Eagle PCB software, and the physical layout design uses off-shelf components including Parallax Propeller Mini, Sparkfun DS3234 RTC, Pololu A4988 Motor Driver, and Sparkfun LCD Screen. However, it is noted that the physical layout design is not limited to using the above components. FIG. 5 shows a circuit diagram for the PCB design.

TABLE 1

| | Description | Source |
|---|---|---|
| Active Components | | |
| Propeller Mini | Microcontroller | Parallax |
| A4988 Stepper | Linear Motor Driver | Pololu |
| DS3234 RTC | High-Accuracy Clock | Sparkfun |

TABLE 1-continued

| | Description | Source |
|---|---|---|
| ADM1602K Screen | LCD Screen | Sparkfun |
| S LCD Backpack | Serial Driver for Screen | Sparkfun |
| 6.25 MHz Crystal | Microcontroller Crystal | Parallax |
| Passive Components | | |
| ¼ W Resistors | Industry Standard | Mouser |
| .1 uF Capacitors | Industry Standard | Mouser |
| DC Barrel Jack Plug | 2.1 mm Center Jack | Mouser |
| Momentary Push Button | Mom On/Off | Mouser |
| XLR 4-Pin Male Adapter | Fits Existing Plugs | Mouser |
| 8 lead (Ethernet) Cable | Industry Standard | Mouser |
| Enclosure Boxes | Generic Enclosure | Mouser |
| 6-Wire Cables | Industry Standard | Mouser |
| Printed Circuit Board | 2-Layer | Custom |

TABLE 2

| System Name | Resolution |
|---|---|
| Linear Motor Drive | 0.25 um |
| Processor Clock | 2 sec. year |
| Encoder | 400 counts/rev |

Software

Figure 2:
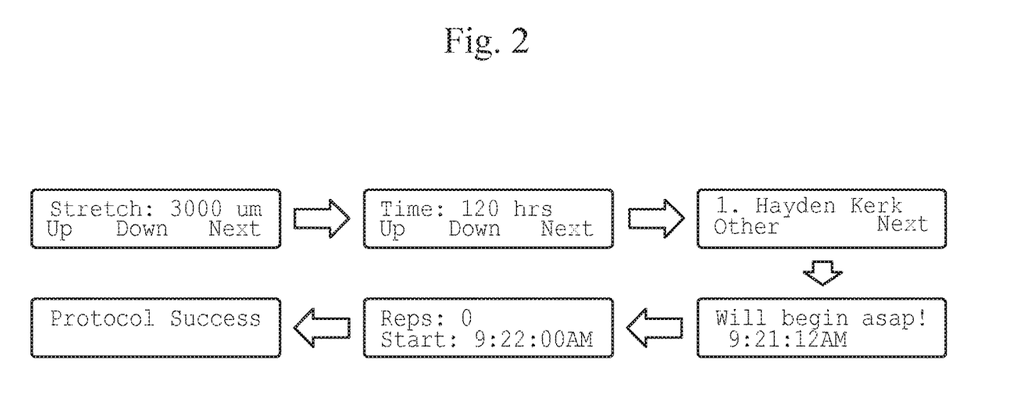
FIG. 2 shows a sample user interface of the bioreactor controller in accordance with another embodiment of the present invention.

In another embodiment, all software for this device is custom written in Parallax's proprietary language; Propeller Spin. In another embodiment, the BrC control code and the expansion creation of the user interface are implemented. Other computer and software code, and languages, and different interfaces may be utilized. The controller device provides a simple user interface (FIG. 2).

It should be appreciated that the device and system discussed herein may take on all shapes along the entire continual geometric spectrum of manipulation of x, y and z planes to provide and meet the structural demands and operational requirements.

It should be appreciated that the related components or portions of the related components port device as discussed herein may take on all shapes along the entire continual geometric spectrum of manipulation of x, y and z planes to provide and meet the environmental and structural demands, and operational requirements.

It should be appreciated that any of the components, devices, or sub-components referred to with regards to any of the present invention embodiments discussed herein, may be integrally or separately formed with one another. Further, redundant functions or structures of the components, sub-components, or devices may be implemented.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

CITATION LIST

The devices, systems, circuits, controllers, apparatuses, materials, compositions, components, computer readable medium, and methods of various embodiments of the invention disclosed herein may utilize aspects disclosed in the following references, applications, publications and patents:

PATENT LITERATURE

1. U.S. Patent Application Publication No. 2009/0265005
2. U.S. Pat. No. 5,795,710

The invention claimed is:

1. A bioreactor controller with a simple user interface comprising:
   a microcontroller configured to:
      select a protocol mode and a setup mode by the user;
      run the protocol mode if the setup mode is not selected by the user;
      stop running the protocol mode for a predetermined time if the protocol mode is selected by the user until the user is completed with calculations and record-keeping;
      detect movement error of the bioreactor controller; and
      inform the error to the user, and
   a linear motor.

2. The bioreactor controller according to claim 1, wherein the detecting movement error is performed by an encoder.

3. The bioreactor controller according to claim 2, wherein a digital, optical, or differential encoder is mounted onto a shaft of the linear motor.

4. The bioreactor controller according to claim 2, wherein the encoder determines whether a shaft of the linear motor of the bioreactor controller moves according to an input command by the user.

5. The bioreactor controller according to claim 1, wherein a temporal accuracy is less than 1 second per week.

6. The bioreactor controller according to claim 1, wherein a resolution of the linear motor is less than 5 µm.

7. A method for a bioreactor controller with a simple user interface, the bioreactor controller comprising a microcontroller and a linear motor, comprising the steps of:
   selecting a protocol mode and a setup mode by the user;
   running the protocol mode if the setup mode is not selected by the user;
   stopping running the protocol mode for a predetermined time if the protocol mode is selected by the user until the user is completed with calculations and record-keeping;
   detecting movement error of the bioreactor controller; and
   informing the error to the user.

8. The method according to claim 7, wherein the detecting movement error is performed by an encoder.

9. The method according to claim 8, wherein a digital, optical, or differential encoder is mounted onto a shaft of the linear motor.

10. The method according to claim 8, wherein the encoder determines whether a shaft of the linear motor of the bioreactor controller moves according to an input command by the user.

11. The method according to claim 7, wherein a temporal accuracy is less than 1 second per week.

12. The method according to claim 7, wherein a resolution of the linear motor is less than 5 µm.

13. A non-transitory computer readable medium storing a program causing a computer to execute a method for a bioreactor controller with a simple user interface, the bioreactor controller comprising a microcontroller and a linear motor, the method comprising the steps of:
   selecting a protocol mode and a setup mode by the user;
   running the protocol mode if the setup mode is not selected by the user;
   stopping running the protocol mode for a predetermined time if the protocol mode is selected by the user until the user is completed with calculations and record-keeping;
   detecting movement error of the bioreactor controller; and
   informing the error to the user.

14. The non-transitory computer readable medium according to claim 13, wherein the detecting movement error is performed by an encoder.

15. The non-transitory computer readable medium according to claim 14, wherein a digital, optical, or differential encoder is mounted onto a shaft of the linear motor.

16. The non-transitory computer readable medium according to claim 14, wherein the encoder determines whether a shaft of the linear motor of the bioreactor controller moves according to an input command by the user.

17. The non-transitory computer readable medium according to claim 13, wherein a temporal accuracy is less than 1 second per week.

18. The non-transitory computer readable medium according to claim 13, wherein a resolution of the linear motor is less than 5 μm.

* * * * *